US005578048A

United States Patent [19]
Pasqualucci et al.

[11] Patent Number: 5,578,048
[45] Date of Patent: Nov. 26, 1996

[54] MANIPULATOR APPARATUS

[75] Inventors: Joseph Pasqualucci, North Haven; David A. Nicholas, Trumbull, both of Conn.

[73] Assignee: United States Surgical Corporation, Norwalk, Conn.

[21] Appl. No.: 368,727

[22] Filed: Jan. 4, 1995

Related U.S. Application Data

[63] Continuation of Ser. No. 122,079, Sep. 15, 1993, abandoned.

[51] Int. Cl.$^6$ ............................................. A61B 17/00
[52] U.S. Cl. ............................................. 606/192
[58] Field of Search ............................ 606/191–195, 606/198; 604/96–104, 41; 128/20; 600/207

[56] References Cited

U.S. PATENT DOCUMENTS

| | | |
|---|---|---|
| 1,620,828 | 3/1927 | Moloney . |
| 1,735,519 | 11/1929 | Vance ........................... 606/196 |
| 2,028,635 | 1/1936 | Wappler . |
| 3,314,431 | 4/1967 | Smith . |
| 3,459,175 | 8/1969 | Miller ........................... 604/96 |
| 3,854,484 | 12/1974 | Jackson . |
| 3,877,433 | 4/1975 | Librach . |
| 3,948,270 | 4/1976 | Hasson . |
| 3,972,331 | 8/1976 | Bolduc et al. . |
| 4,000,743 | 1/1977 | Weaver . |
| 4,022,208 | 5/1977 | Valtchev . |
| 4,085,756 | 4/1978 | Weaver . |
| 4,089,337 | 5/1978 | Kronner . |
| 4,198,981 | 4/1980 | Sinnreich . |
| 4,207,891 | 6/1980 | Bolduc . |
| 4,245,639 | 1/1981 | La Rosa . |
| 4,430,076 | 2/1984 | Harris . |
| 4,439,185 | 3/1984 | Lundquist . |
| 4,459,978 | 7/1984 | Kotsanis . |

(List continued on next page.)

FOREIGN PATENT DOCUMENTS

| | | |
|---|---|---|
| 504528 | 10/1979 | Australia . |
| 0217559 | 4/1987 | European Pat. Off. . |
| 0259582 | 3/1988 | European Pat. Off. . |
| 400458 | 12/1990 | European Pat. Off. . |
| 0557806 | 9/1993 | European Pat. Off. . |
| 1402043 | 10/1965 | France . |
| 0990220 | 1/1993 | U.S.S.R. . |
| WO92/21298 | 12/1992 | WIPO . |

OTHER PUBLICATIONS

Richard Wolf Catalog (pp. E–37, E–38) 1989.
Corson, Stephen L., "Two New Laparoscopic Instruments: Bipolar Sterilizing Forceps and Uterine Manipulator" in *Medical Instrumentation*, vol 11, No. 1, 1977.
Unimar Product Brochure (1993).
Product Brochure for Zumi 4.5™ and Zui–4.0™ uterine manipulators from catalog of Cabot Medical (corresponds to U.S. Pat. 4,430,076).
Product Brochure for Zumi–4.5™ uterine manipulator from catalog of Progressive Medical Technology, Inc. (pp. 1148–1151).

*Primary Examiner*—Michael Powell Buiz
*Assistant Examiner*—William W. Lewis

[57] ABSTRACT

A surgical apparatus for manipulating bodily tissue includes a handle member, an elongated member connected to the handle member and extending distally therefrom, a fluid expandable member supported at a distal end portion of the elongated member and a fluid dispensing mechanism in fluid communication with the expandable member for selectively incrementally dispensing inflation fluid into the expandable member to selectively incrementally inflate the expandable member. The distal end portion of the elongated member is adapted to articulate relative to a longitudinal axis defined by the remaining portion of the elongated member such that the expandable member is pivotal therewith. A control mechanism is provided to selectively control articulation of the distal end portion of the elongated member.

27 Claims, 11 Drawing Sheets

U.S. PATENT DOCUMENTS

| | | |
|---|---|---|
| 4,559,944 | 12/1985 | Jaeger . |
| 4,585,438 | 4/1986 | Makler . |
| 4,598,699 | 7/1986 | Garren et al. . |
| 4,664,114 | 5/1987 | Ghodsian . |
| 4,723,938 | 2/1988 | Goodin et al. . |
| 4,802,479 | 2/1989 | Haber et al. . |
| 4,832,692 | 3/1989 | Box et al. ................................ 604/99 |
| 4,865,587 | 9/1989 | Walling . |
| 4,872,456 | 10/1989 | Hasson . |
| 4,872,483 | 10/1989 | Shah . |
| 4,880,015 | 11/1989 | Nierman . |
| 4,919,121 | 4/1990 | Rydell et al. ............................ 604/97 |
| 4,944,726 | 7/1990 | Hilal et al. . |
| 4,966,583 | 10/1990 | Debbas . |
| 4,997,419 | 3/1991 | Lakatos et al. . |
| 5,007,898 | 4/1991 | Rosenbluth et al. . |
| 5,015,233 | 5/1991 | McGough et al. . |
| 5,037,430 | 8/1991 | Hasson . |
| 5,071,407 | 12/1991 | Termin et al. . |
| 5,084,060 | 1/1992 | Freund et al. . |
| 5,104,377 | 4/1992 | Levine . |
| 5,135,488 | 8/1992 | Foote et al. . |
| 5,147,300 | 9/1992 | Robinson et al. . |
| 5,163,949 | 11/1992 | Bonutti . |
| 5,178,133 | 1/1993 | Pena . |
| 5,195,507 | 3/1993 | Bilweis . |
| 5,195,964 | 3/1993 | Kletzky . |
| 5,197,971 | 3/1993 | Bonutti . |
| 5,209,731 | 5/1993 | Sterman et al. . |
| 5,209,747 | 5/1993 | Kroepfler . |
| 5,209,754 | 5/1993 | Ahluwalia . |
| 5,217,466 | 6/1993 | Hasson . |
| 5,224,931 | 7/1993 | Kumar . |
| 5,237,985 | 8/1993 | Hodgson et al. . |
| 5,248,304 | 9/1993 | Vigdorchik et al. . |
| 5,318,586 | 6/1994 | Ereren . |
| 5,331,975 | 7/1994 | Bonutti . |
| 5,382,252 | 1/1995 | Failla et al. . |
| 5,400,773 | 3/1995 | Zhu et al. ................................ 600/207 |
| 5,445,643 | 8/1995 | Valtchev . |

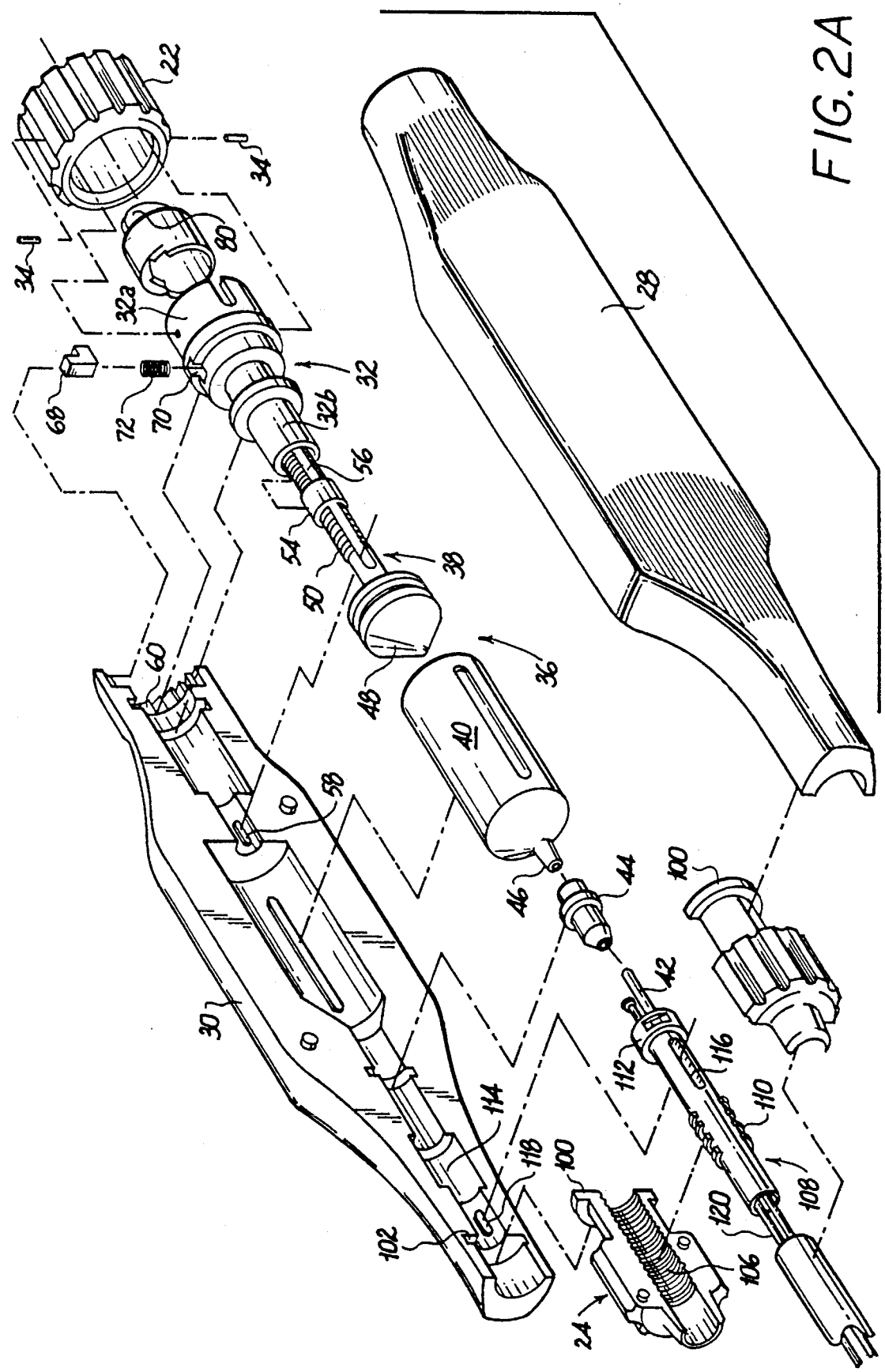

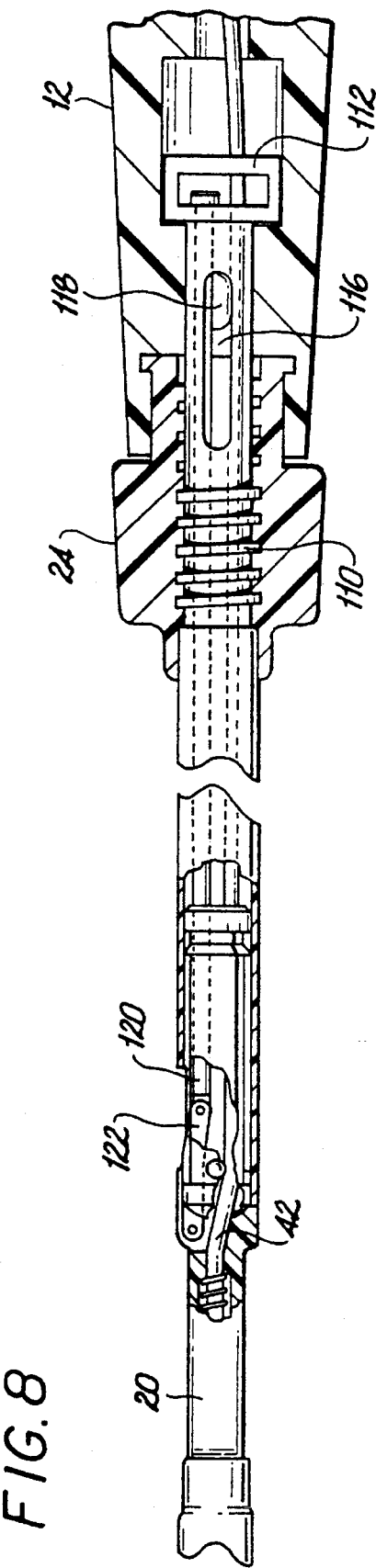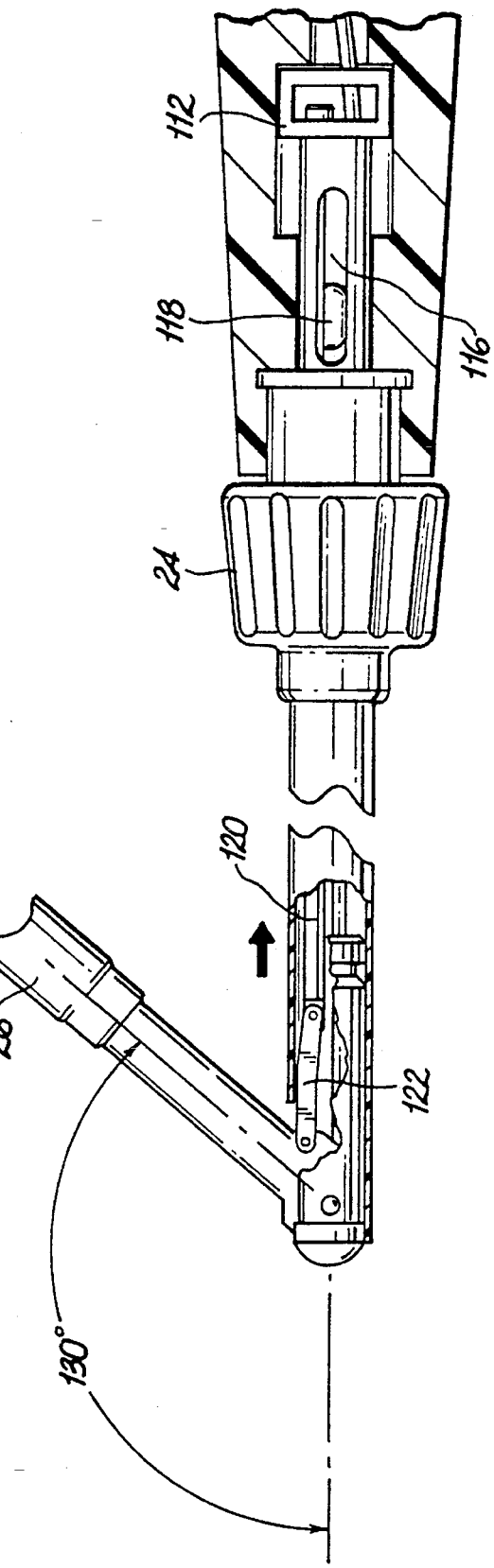
FIG. 8
FIG. 9

MANIPULATOR APPARATUS

This is a continuation, of application Ser. No. 08/122,079 filed on Sep. 15, 1993, now abandoned.

BACKGROUND OF THE INVENTION

1. Field of the Invention

The present invention relates to an apparatus for manipulating body tissue during surgical operations and, more specifically, to an apparatus for manipulating a uterus for examination of the uterine cavity during surgical procedure.

2. Description of the Prior Art

Laparoscopic and endoscopic surgery has been widely accepted as the preferred surgical procedure for treatment of a variety of disorders that were formally treated by conventional surgical techniques. In laparoscopic procedures, surgery is performed in the interior of the abdomen through a small incision; in endoscopic procedures, surgery is performed in any hollow viscus of the body through narrow endoscopic tubes inserted through small entrance wounds in the skin.

In conjunction with laparoscopic surgery, pneumoperitoneum gases are generally introduced into the peritoneal cavity to expand the cavity and raise the cavity wall away from the vital organs therein. Thereafter, a trocar, which is a sharp pointed instrument, is inserted into a cannula assembly and used to puncture the inner lining of the peritoneal cavity. The trocar is withdrawn and a laparoscopic surgical instrument is inserted through the cannula to perform the desired surgery.

Laparoscopic and laparoscopically assisted surgical techniques are currently being performed in operative procedures involving the uterus, such as, for example, examination of the uterus for the purpose of sterilization, or, for investigating tubal patency in cases of infertility or for laparoscopically assisted vaginal hysterectomy procedures. In such techniques, it is often necessary to manipulate or reposition the uterus in order to gain visual and tactile access to different areas of the uterus and the surrounding organs.

Prior art devices for manipulating or repositioning the uterus include uterine grasping forceps which enable the surgeon to firmly grasp the uterine cervix and manipulate it to a desired position. However, due to the narrow configuration of the forceps jaws, such manipulation can result in injury to the uterus including penetration of the uterine wall or tearing surrounding tissue.

Another type of uterine manipulator device includes a catheter having an inflatable or hollow balloon member at a distal end thereof. The catheter is introduced within the cervix and the balloon is inflated to engage the uterine wall to position the uterus for examination purposes. Although the devices incorporating inflatable balloons have proven to be less invasive than the aforementioned conventional forceps devices, these devices have their own particular shortcomings. For example, the prior art balloon devices known heretofore fail to provide a mechanism which enables the surgeon to readily and incrementally control the level of inflation of the balloon.

Accordingly, the present invention is directed to an apparatus which obviates the inherent disadvantages of known manipulators by providing a minimally obtrusive manipulating instrument which features an enhanced level of control over inflation of the balloon or expandable member as well as improving access to the organs or tissue in the body cavity.

SUMMARY OF THE INVENTION

Generally stated, the present invention is directed to a surgical apparatus for manipulating body tissue. The apparatus comprises a handle member, an elongated member connected to the handle member and extending distally therefrom, an expandable member supported at a distal end portion of the elongated member and fluid dispensing means in fluid communication with the expandable member for selectively incrementally dispensing inflation fluid into the expandable member to selectively incrementally inflate the expandable member. The distal end portion of the elongated member may be adapted articulate relative to a longitudinal axis defined by the remaining portion of the elongated member such that the expandable member is pivotal therewith. Preferably, the fluid expandable member is supported by a support member connected to the distal end portion of the elongated member. The support member is selectively articulatable by a control member disposed at a proximal location.

In one embodiment, a supply of inflation fluid, i.e. liquid or gas, is contained in a chamber in a frame member and a plunger axially movable within the chamber is provided for dispensing the fluid. The elongated member includes an inflation lumen in communication with the chamber of the frame member. Plunger advancing means is provided for selectively incrementally advancing the plunger within the chamber to dispense inflation fluid through the inflation lumen and into the expandable member to selectively incrementally inflate the expandable member.

Preferably, the plunger advancing means is actuated by a control knob rotatably mounted to the frame member and operatively connected to the plunger such that rotational movement of the control knob in first and second directions causes corresponding respective distal and proximal axial movement of the plunger. The control knob is operatively associated with a ratchet and associated pawl mechanism to permit rotational movement of the control knob in the first direction while preventing rotational movement of the control knob in the second direction. Means is provided for selectively releasing the ratchet and associated pawl mechanism to permit rotational movement of the control knob in the second direction thereof to axially move the plunger in the proximal direction.

The preferred release means comprises a release member rotatably mounted to the frame member and engagable with the pawl member whereby rotational movement of the release member through a first angular section of rotation causes the pawl member to move to the second position disengaged from the ratchet member. The release member is adapted to permit the pawl member to return to the first position in engagement with the ratchet member upon rotation of the release member through a second angular section of rotation.

The preferred articulation control means comprises a rotatable member mounted about the proximal end portion of the elongated member and adapted to reciprocally rotate relative to the elongated member. The rotatable member is operatively connected to an elongated control rod positioned within the elongated member, whereby rotational movement of the rotatable member in a first direction causes longitudinal movement of the elongated control rod in a proximal direction and rotational movement of the cylindrical rotatable member in a second direction causes longitudinal movement of the elongated control rod in a distal direction. The elongated control rod is operatively connected to the support member such that longitudinal movement of the elongated control rod in the proximal and distal directions causes corresponding articulation movement of the support member.

In an alternate embodiment, the endoscopic portion of the instrument is curved to improve access to the tissue site.

BRIEF DESCRIPTION OF THE DRAWINGS

The accompanying drawings, referred to herein and constituting a part hereof, illustrate preferred embodiments of the present invention and together with the description, serve to explain the principles of the present invention, wherein:

FIG. 2A is an exploded perspective view with parts separated of the handle of the apparatus of FIG. 1;

FIG. 8 is a partial cross-sectional view illustrating the apparatus in the non-articulated position;

FIG. 9 is a partial cross-sectional view illustrating the apparatus in the articulated position;

FIG. 12A is a cross-sectional view of the distal end portion of the apparatus of FIG. 11 illustrating the expandable member in an inflated condition; and.

DETAILED DESCRIPTION OF THE PREFERRED EMBODIMENTS

The present invention is contemplated to be used in surgical procedures where manipulation of body structures is required to provide access to the particular body structure or adjacent body structures. While the apparatus of the present invention is particularly useful for manipulation of the uterus such as in hysterectomy procedures, it will also be useful for treating other body organs and structures during other laparoscopic and non-laparoscopic surgical procedures. For example, the apparatus of the present invention may be effectively used in gastrectomy procedures, manipulation of the intestinal organs during bowel resection and manipulation of the gall bladder during a laparoscopic cholecystectomy procedure.

Figure 1:
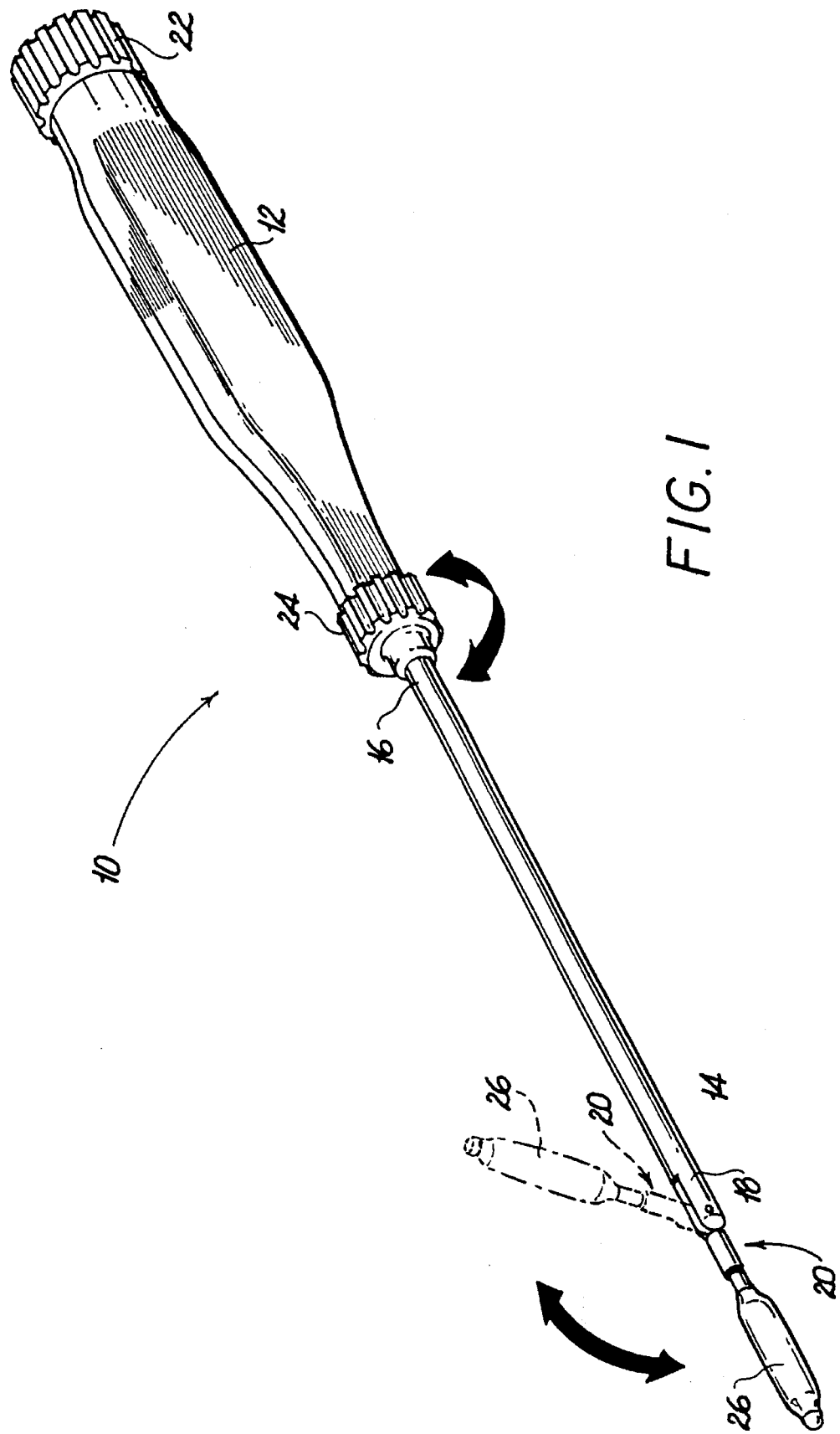
FIG. 1 is a perspective view of one embodiment of the manipulator apparatus constructed in accordance with the present invention.

Referring now to FIG. 1, there is illustrated in perspective view one embodiment of the manipulator apparatus constructed according to the present invention. Apparatus 10 includes a handle or frame 12 and an elongated tubular or endoscopic portion 14 extending distally from the frame 12. Endoscopic portion 14 includes proximal end portion 16 and distal end portion 18. An expandable balloon member 26 is located at distal end position 18 to help maintain the apparatus in position in the body. Attached to distal end portion 18 is an articulating support member 20 which is adapted to articulate with respect to the longitudinal axis extending centrally through the endoscopic portion 14. Generally, the articulating support member 20 will selectively articulate up to about 130 degrees with respect to the longitudinal axis of endoscopic portion 14. The articulating support member 20 is shown in FIG. 1, in general alignment with the longitudinal axis of the endoscopic portion 14 and in phantom at a position about 130 degrees relative to the axis to illustrate the range of movement of the support member 20. Articulating control knob 24, mounted to the distal end of the Frame 12, rotates about proximal end portion 16 of endoscopic portion 14 to position articulating support member 20 at selected angular orientations relative to the longitudinal axis of the endoscopic portion An inflation control knob 22 is rotatably mounted to the proximal end of frame 12. Inflation control knob 22 is adapted to rotate to selectively inflate the expandable balloon member 26 supported by support member 20.

Referring now to FIG. 2A, the operating components of frame 12 of the apparatus will be discussed in detail. Frame 12 includes housing half sections 28, 30. The housing half sections 28, 30 are formed of a suitable plastic material such as polycarbonate, polyethylene or the like and are normally attached along the seam by suitable attachment techniques such as adhesive, ultrasonic welding, screws or the like. Inflation control knob 22 is generally cylindrically shaped and is adapted to rotate about the proximal end of frame 12, i.e, about the longitudinal axis of frame 12. Inflation control knob 22 is operatively connected to internal sleeve 32 which is mounted for rotational movement within the interior of handle 12 such that rotation of control knob 22 in one direction causes corresponding rotation of the internal sleeve 32 in the same direction. This rotation of internal sleeve 32 drives screw 50 longitudinally as described below. Internal sleeve 32 includes proximal end portion 32a and threaded distal end portion 32b of lesser diameter than proximal end portion 32a. The proximal end portion 32a of internal sleeve 32 is received within the interior of control knob 22 and is connected to the control knob by pins 34 which are received within correspondingly positioned and aligned apertures in the knob 22 and sleeve 32 as shown (see also FIG. 3). Other alterative methods for securing these two components may be readily determined by one skilled in the art.

Figure 2B:
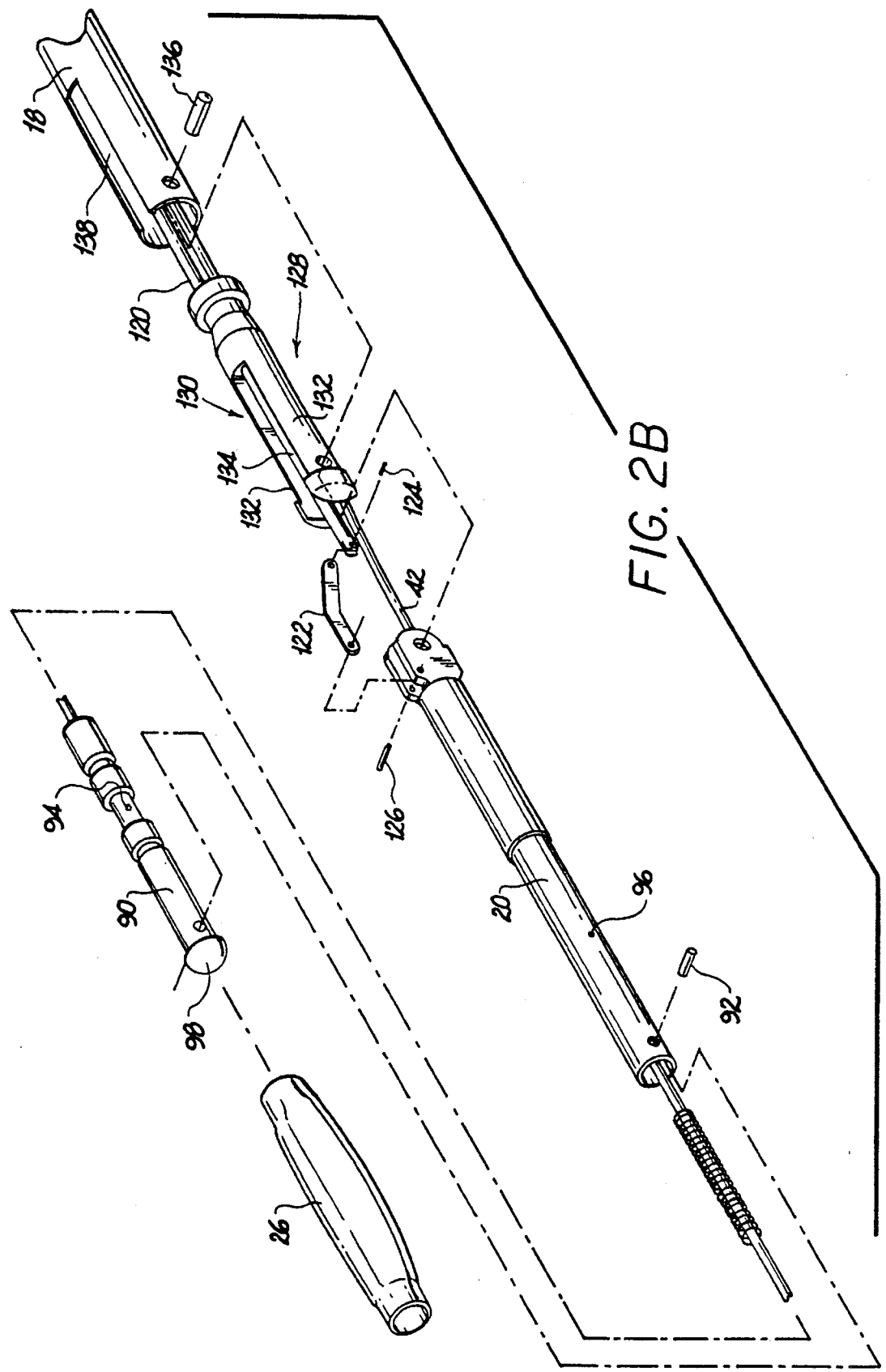
FIG. 2B is an exploded perspective view with parts separated of the endoscopic portion of the apparatus of FIG. 1.
Figure 3:
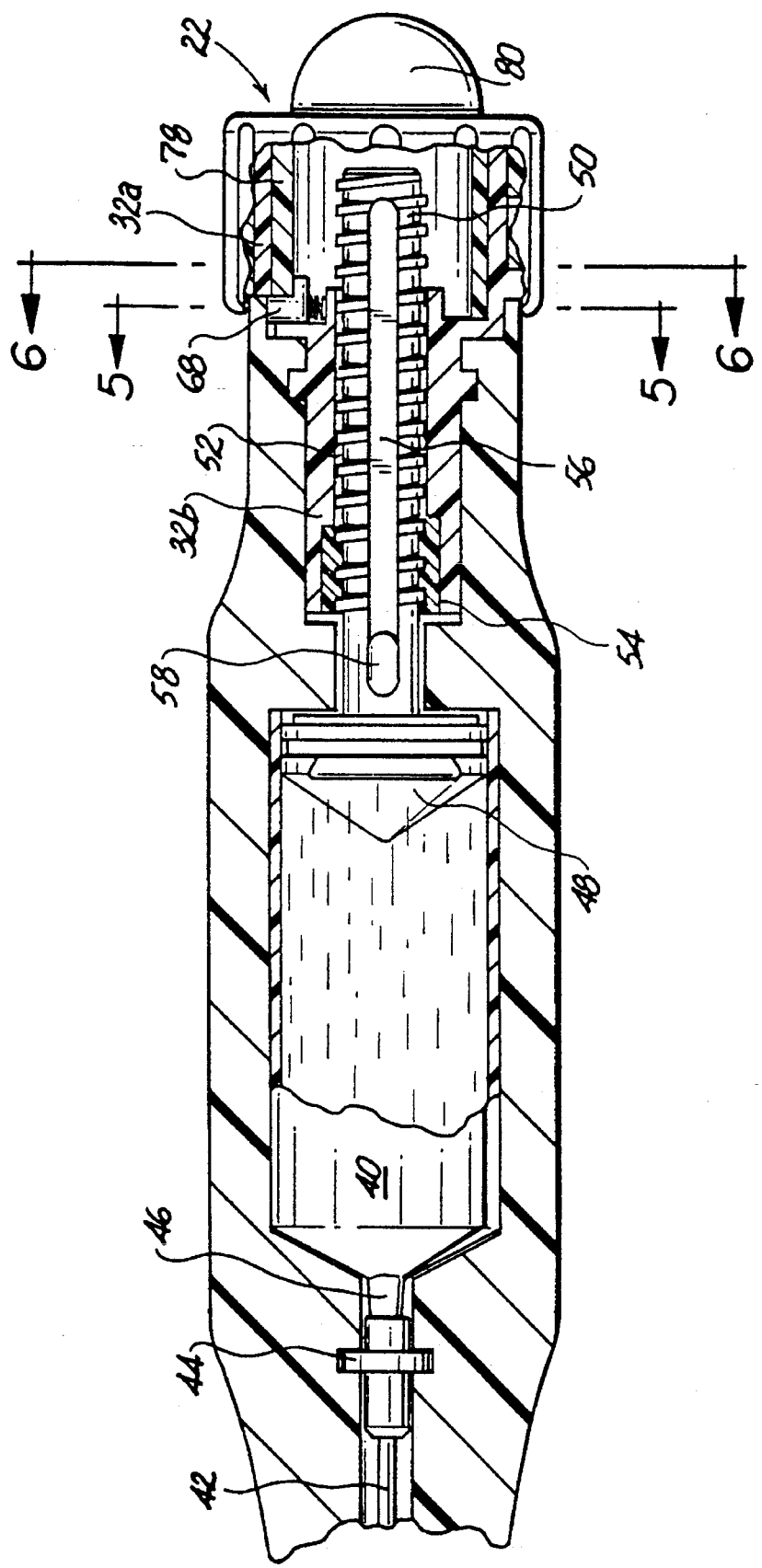
FIG. 3 is a partial cross-sectional view further illustrating the operating components of the handle of FIG. 2A.
Figure 4:
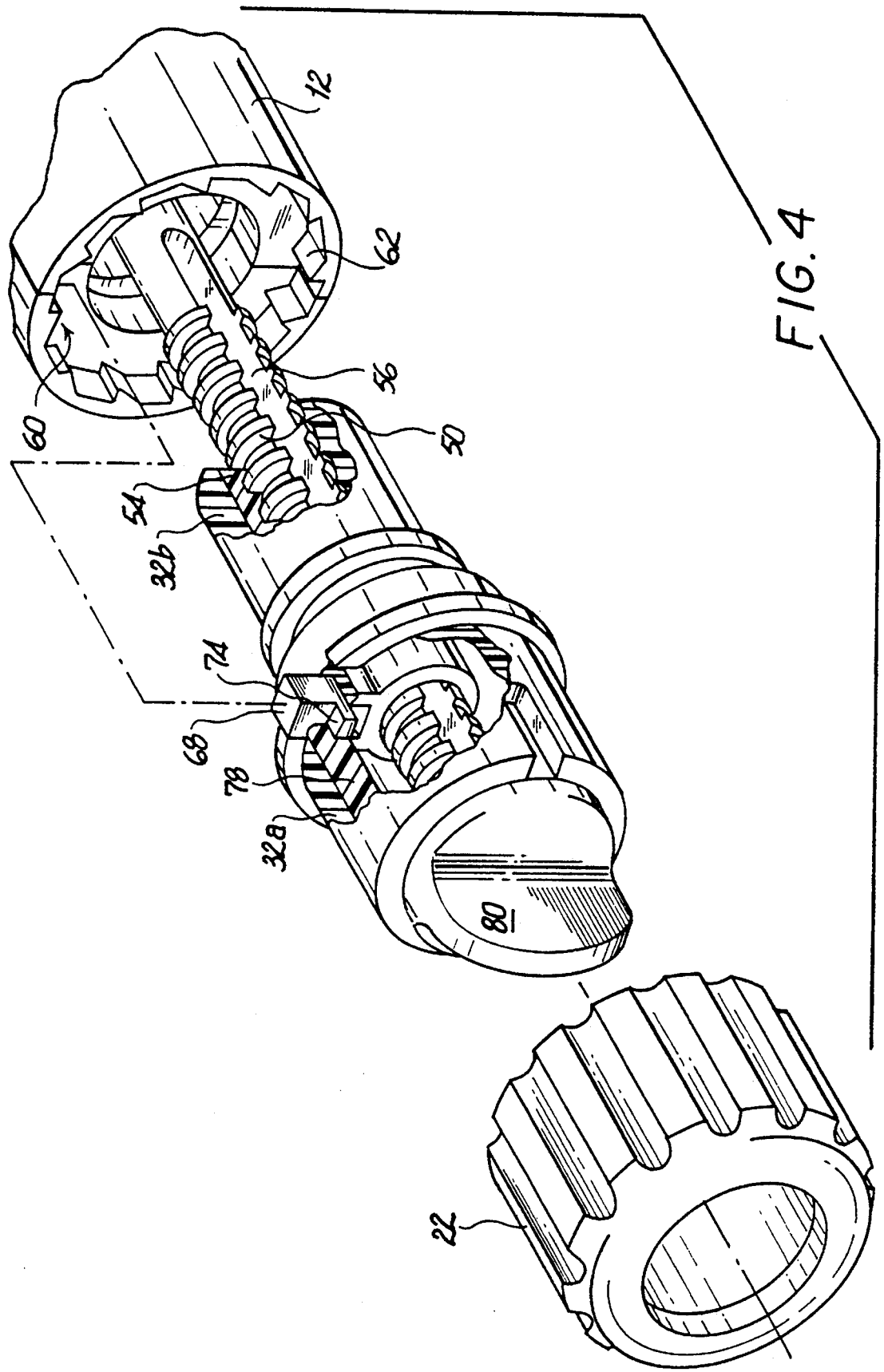
FIG. 4 is an exploded perspective view with parts separated illustrating the ratchet mechanism for providing controlled inflation of the expandable member.

Referring now to FIG. 2A, in conjunction with FIGS. 3 and 4, a syringe assembly 36 including plunger 38 and associated plunger housing 40 is disposed in the approximate center of frame 12. Plunger 38 is axially movable within plunger housing 40 to direct the inflation fluids stored within the housing 40 into expandable member 26 via inflation lumen 42 extending within endoscopic portion 14. A connector member 44 connects the distal outlet portion 46 of plunger housing 40 to inflation lumen 42.

Plunger 38 includes plunger head 48 attached to plunger drive screw 50 as shown. Plunger head 48 can be made of an elastoneric material to act as a seal within housing 40, or alternately a separate sealing member, such as an elastoneric 0-ring can be positioned over plunger head 48. Plunger drive screw 50 includes a peripheral threaded portion which is received within the longitudinal bore 52 of the distal end portion 32b of internal sleeve 32 (FIG. 3). A tapped insert 54 is positioned on drive screw 50 and includes internal threads which correspondingly mesh with the threaded portion of drive screw 50. Tapped insert 54 is securely mounted to the interior of the distal end portion 32b of internal sleeve 32 by conventional means such as with the use of adhesives or the like, and, thus, rotates with the sleeve 32 upon rotation of control knob 22. Alternatively, tapered insert 54 can be integral with sleeve 32, i.e. molded thereon.

Drive screw 50 includes a channel 56 extending generally longitudinally along its axis. Channel 56 is dimensioned to receive projections 58 integrally formed with the interior surfaces of frame 12 and extending therefrom. Projections 58 prevent plunger drive screw 50 from rotating when internal sleeve 32 and tapped insert 54 are rotated. Accordingly, as internal sleeve 32 and insert 54 rotate in response to corresponding rotational movement of inflation control knob 22, plunger 38 moves axially due to the corresponding respective threaded engagement of the insert 54 and the drive screw 50.

Referring now to FIG. 2A in conjunction with FIGS. 4 and 5, the ratchet mechanism of the apparatus will be described. The ratchet mechanism serves essentially two functions: 1) it provides for selective controlled movement of plunger 38 so as to selectively and incrementally control the level of inflation of expandable member 26; and 2) it prevents undesired rotation of control knob 22 in a negative direction so as avoid undesired proximal movement of plunger 38 and corresponding deflation of expandable member 26. The components of the ratchet mechanism include the proximal end of frame 12 which has an interior ratchet surface 60 (FIG. 4) defined by a plurality of successive ratchet teeth 62 having inclined camming surfaces 64 separated by transverse surfaces 66 as shown in the cross-sectional view of FIG. 5. A pawl 68 received within a rectangular housing channel 70 formed in the proximal end portion 32a of internal sleeve 32 is positioned to engage the ratchet teeth 62. Pawl 68 is adapted to reciprocally move into and out of engagement with the ratchet surface 60 of frame 12 and is biased to the engaged position by coil spring 72 which is received within the hollow interior of pawl 68 and normally biases the pawl 68 away from the central axis of frame 12 into engagement with the ratchet surface 60. Pawl 68 further includes an inclined camming shelf 74 (FIG. 4) disposed at the approximate midsection thereof, the importance of which will become apparent from the description provided below.

Figure 5:
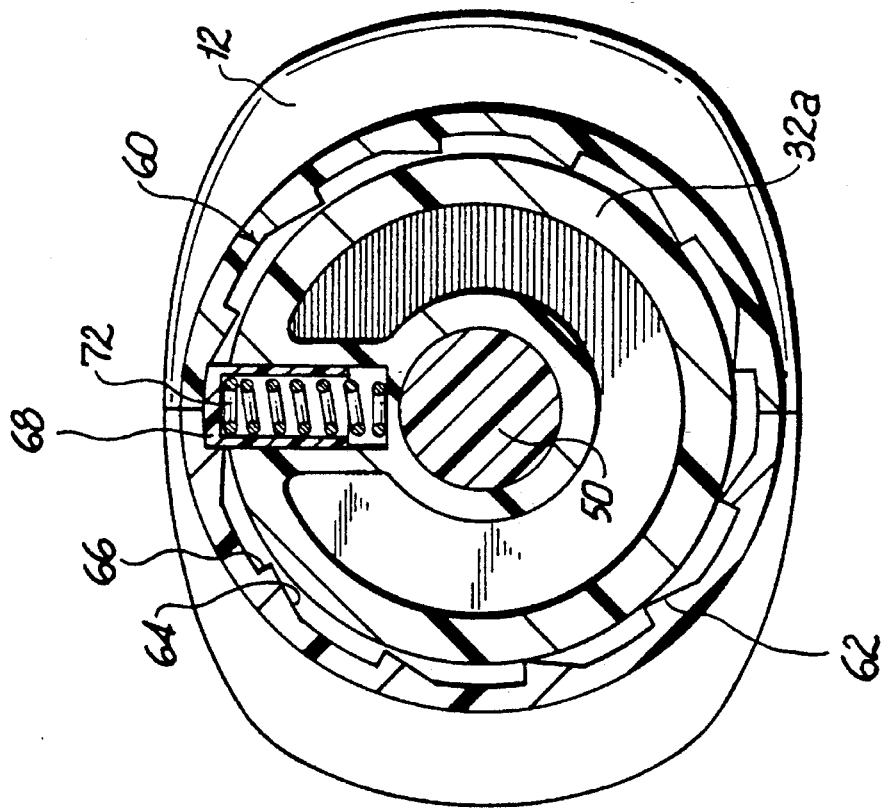
FIG. 5 is a cross-sectional view taken along the lines 5—5 of FIG. 3 further illustrating the operative components of the ratchet mechanism.

Referring particularly to the cross-sectional view of FIG. 5, the successive arrangement of ratchet teeth 62 provide a means to advance plunger 38 at selected incremental predetermined distances. In particular, as control knob 22 is rotated in a clockwise direction, which causes corresponding clockwise movement of internal sleeve 32, camming surface 64 of ratchet teeth 62 causes pawl 68 to be driven towards the center axis of frame 12 against the force of spring 72. Upon clearing camming surface 64, pawl 68 is forced under the influence of spring 72 to its normal engaged position. Each successive rotation of control knob 22 and internal sleeve 32 through an incremental sector of rotation cause pawl 68 to clear a single ratchet tooth 62 advances plunger 38 a predetermined distance. Further, each time pawl 68 clears camming surface 64 of a respective single tooth 62, the pawl 68 snaps back into the engaged position with ratchet surface 60. This return of pawl 68 to its engaged position provides a perceptible tactile and audible indicator to the user that control knob 22 has been rotated through the predetermined sector and, accordingly, plunger 38 has been advanced a predetermined distance. Thus, the operator can selectively incrementally control the axial advancement of plunger 38 by monitoring the number of clicks which correspond to each return of pawl 68 to the engaged position. Control of the plunger 38 controls the degree of inflation of the balloon which not only prevents over inflation but enables the balloon to be inflated to various dimensions to accommodate the size of the patient.

Referring still to FIG. 5, the inclination of camming surfaces 64 permits internal sleeve 32 and control knob 22 to rotate in a clockwise direction only. In particular, internal sleeve 32 is prevented from counterclockwise rotational movement due to engagement of pawl 68 with each transverse bearing surface 66 of the ratchet surface 60. Thus, during inflation of expandable member 26, the control knob 22 can be rotated in one direction only (i.e., a clockwise direction) which corresponds to inflating the expandable member 26. Accordingly, undesired rotating of control knob 22 in the direction corresponding to deflation of expandable member 26 (i.e., counterclockwise direction) is prevented.

Referring now to FIGS. 2A, 3, 4 and 6, the mechanism for releasing the ratchet mechanism will be described. A release member 76 is mounted at the proximal end portion of frame 12 and is adapted to rotate to release the engagement of pawl 68 with the ratchet surface 60 of frame 12. Release member 76 includes a generally interior cylindrical portion 78 which is received within the interior of the proximal end 32a of internal sleeve 32 and a grasping portion 80 which extends outwardly beyond the control knob 22 in a position to be grasped by the user as depicted in FIG. 3. The cylindrical portion 78 of release member 76 includes an inner peripheral surface 82 which defines an irregular surface as best shown in the cross-sectional view of FIG. 6. The irregular surface includes first and second inclined camming surfaces 84, 86 respectively. In the engaged position of pawl 68 with ratchet surface 60, the first camming surface 84 of cylindrical portion 78 contacts shelf 74 of pawl 68. When release member 76 is rotated in a counterclockwise direction by rotating the grasping portion 80 through a predetermined section of rotation, the inclined configuration of first camming surface 84 engages shelf 74 of pawl 68 and forces the pawl 68 toward the central axis of frame 12 out of engagement with ratchet surface 60. Accordingly, control knob 22 is free to rotate in either direction. Thus, once the pawl 68 is disengaged, the surgeon may quickly rotate control knob 22 in a positive clockwise direction to rapidly inflate expandable member 26 or in a negative counterclockwise direction to return the plunger 38 to its initial unadvanced position and deflate the expandable member. FIG. 7 illustrates release member 76 rotated to disengage pawl 68 from ratchet surface 60.

Figure 6:
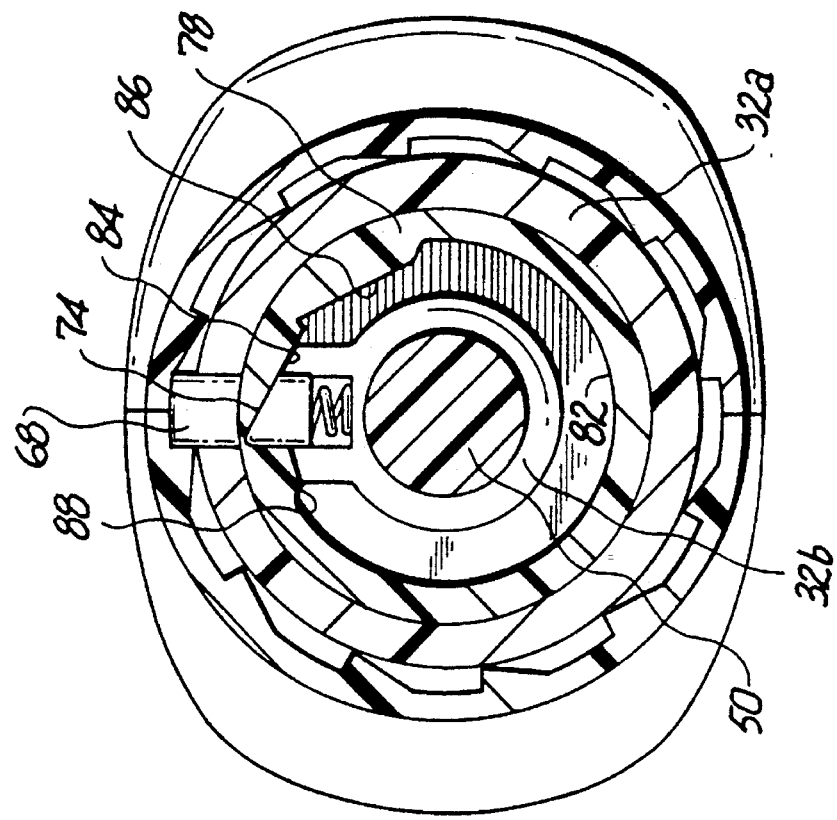
FIG. 6 is a cross-sectional view taken along the lines 6—6 of FIG. 3 illustrating the release mechanism for releasing the ratchet mechanism.
Figure 7:
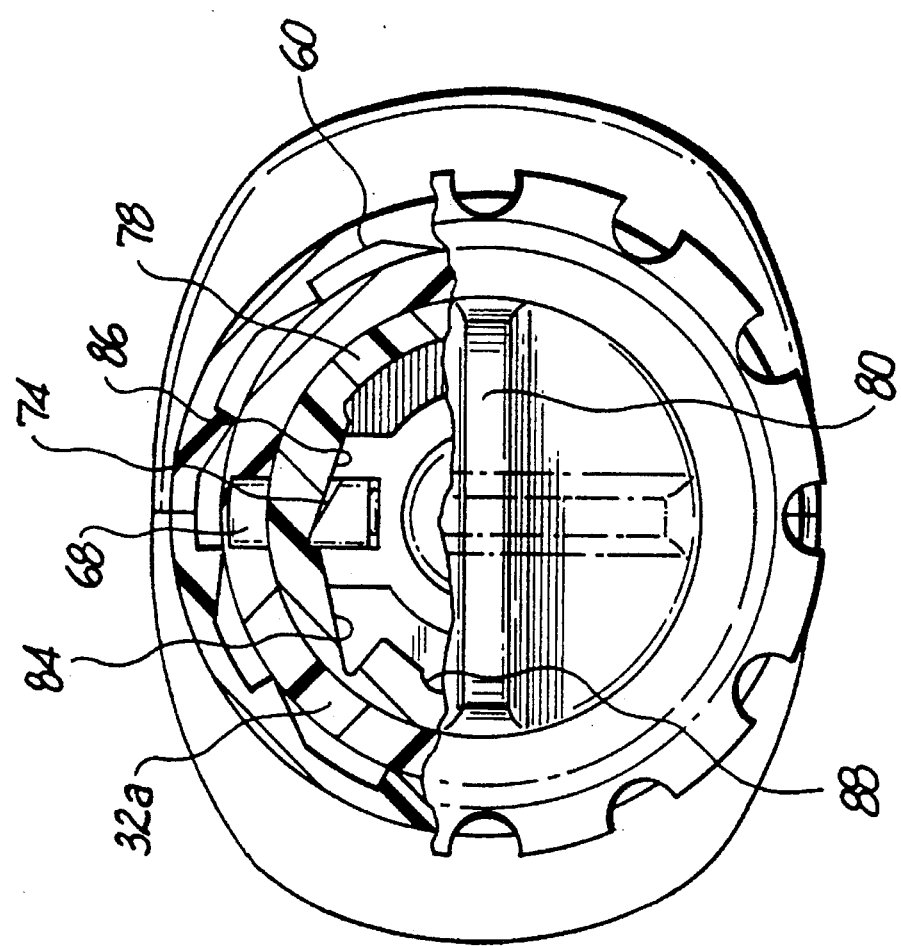
FIG. 7 is a view similar to the cross-sectional view of FIG. 6 illustrating the release mechanism actuated to release the ratchet mechanism.

Referring to FIGS. 6 and 7, the ratchet mechanism is returned to its engaged position by continued rotation of release member 76 in the counterclockwise direction such that shelf 74 of pawl 68 clears second camming surface 86 and encounters inclined surface 88. Inclined surface 88 forces the pawl 68 towards the central axis of frame 12 due to engagement with shelf 74 whereby the pawl 68 is positioned in the position shown in FIG. 6 in engagement with ratchet surface 60 of frame 12.

Referring now to FIG. 2B, the remaining components of the inflating mechanism include inflation lumen 42 which extends through endoscopic portion 14 and support member 20, and is connected to diffusing element 90. Inflation lumen 42 is preferably readily flexible to accommodate the repetitive flexing it undergoes during articulating movement of support member 20. Diffusing element 90 is disposed within the distal end portion of support member 20 and is connected to the support member by mounting pin 92 which extends through correspondingly positioned apertures formed in the two components as shown. Diffusing element 90 includes an aperture 94 at its general midportion which is in general alignment with aperture 96 formed in the distal end portion of articulating support member 20. Aperture 94 releases the inflation fluids ejected by the plunger assembly, which fluids are released through aperture 96 of support member 20 and into expandable member 26 positioned on the distal end portion of articulating support member 20 to expand the member. The distal end portion of diffusing element 90 defines a rounded tip 98 of a soft material to avoid trauma to the cervical canal and the uterus during insertion of the apparatus.

Figure 10:
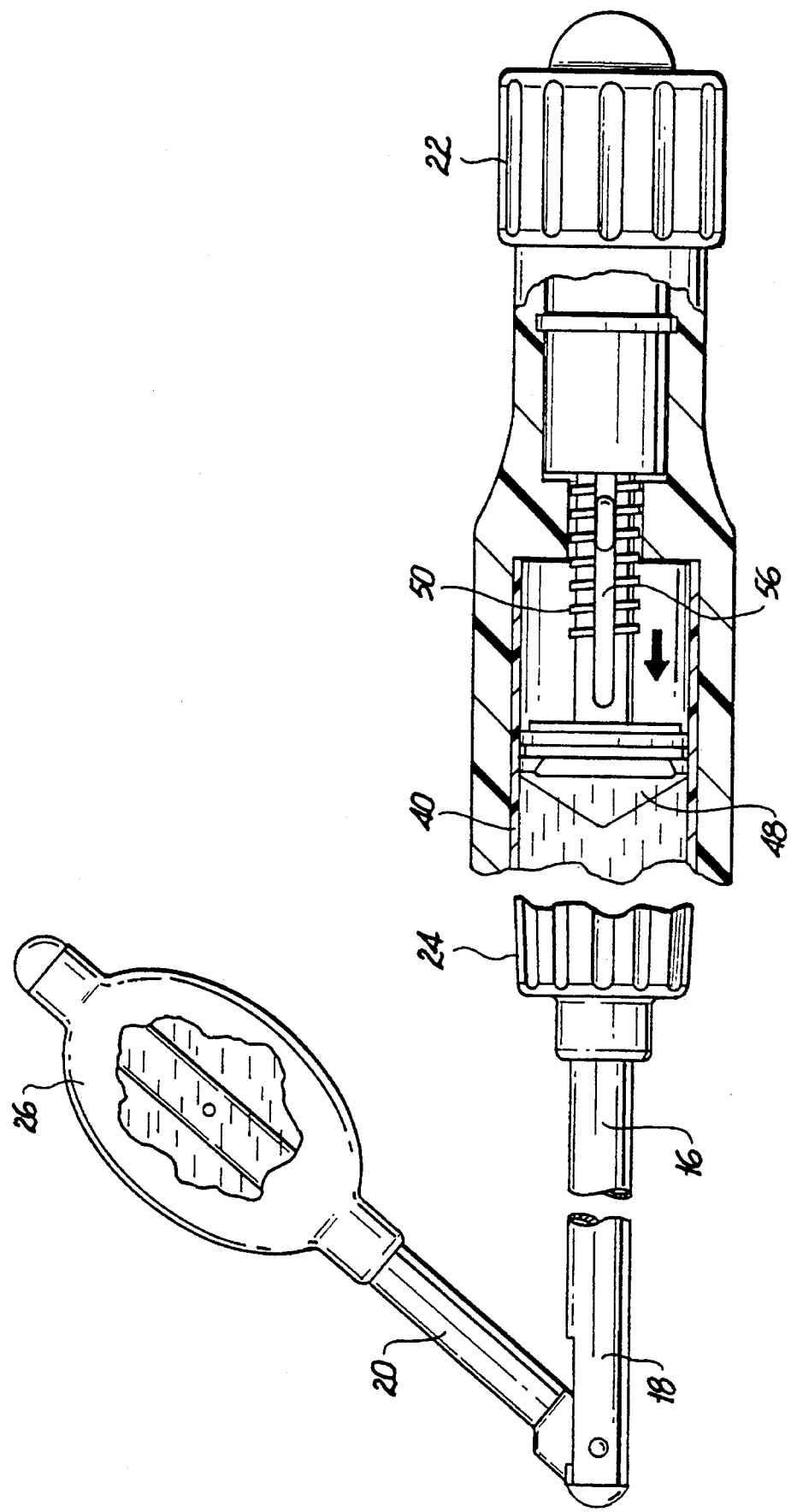
FIG. 10 is a cross-sectional view of the apparatus in the articulated position and the expandable member in an inflated condition.

As previously mentioned, expandable member 26, e.g. a balloon, is positioned on the distal end portion of support member 20. The proximal and distal end portions of expandable member 26 are dimensioned to tightly fit about support member 20 such that a fluid tight seal is formed between the support member 20 and the expandable member 26. Expandable member 26 is preferably formed of an elastomeric material such as polyurethane and in the preferred embodiment can be filled to a volume capacity of about 30 cc. Clearly, expandable member of other capacities can be utilized. The inflation fluids used to expand expandable member 26 may be water, a saline solution, gases such as air, or any other fluid, i.e. flowable substance, suitable for such purposes. FIG. 10 illustrates expandable member 26 in an inflated condition.

Referring now to FIGS. 2A, 2B, 8 and 9, the mechanism for providing articulating movement to support member 20 attached to the distal end portion 18 of endoscopic portion 14 will be described. Articulating control knob 24 is mounted to the distal end of frame 12 for rotational movement about the proximal end portion 16 of endoscopic portion 14. Articulating control knob 24 includes a circumferential flange portion 100 at its proximal end which is received within a correspondingly dimensioned recess 102 formed in frame half sections 28,30 to rotatably mount the knob 24 to the frame. Articulating control knob 24 also includes a longitudinal bore 104 with an internal threaded portion 106.

Drive sleeve 108 is disposed within bore 104 of articulating control knob 24 and includes an external threaded portion 110 which cooperatively meshes with the internal threaded portion 106 of control knob 24. The proximal end of drive sleeve 98 includes a circumferential collar 112 which defines a diameter which is greater than the diameter of the remaining portion of the sleeve 108. Collar 112 of drive sleeve 108 is received within a correspondingly dimensioned annular recess 114 formed in the frame haft sections 28,30 to mount the sleeve 108 to the frame 12. Drive sleeve 108 is capable of longitudinal movement in response to rotational movement of articulating control knob 24 due to the engagement of the respective threaded portions of the drive sleeve 108 and the knob 24. A longitudinal channel 116 is formed in drive sleeve 108 which receives an elongated projection 118 extending from the interior surfaces of each frame section 26, 28 to ensure the drive sleeve 108 does not rotate along with the articulating control knob 24.

An elongated rod member 120 extends within the interior of drive sleeve 108 and the interior of endoscopic portion 14. Rod member 120 is connected at its proximal end to circumferential collar 112 of drive sleeve 108 and at its distal end to linkage member 122 (FIG. 2B) via linkage pin 124. Linkage member 122 is connected to support member 20 via linkage pin 126. Rod member 120 moves axially along with drive sleeve 108 in response to rotational movement of articulating control knob 24. Axial movement of rod 120 member controls the articulation of support member 20, i.e., proximal movement of rod member 120 pivots the support member within a desired degree of rotation. Distal movement of the rod member 120 moves the support member 20 towards the generally aligned position shown in FIG. 1.

As shown in FIG. 2B, a sleeve member 128 is positioned within the distal end portion 18 of endoscopic portion 14. Sleeve member 128 includes a yoke portion 130 having a pair of opposed depending arms 132 which define a channel 134. In the assembled condition, sleeve member 128 is positioned within distal end portion 18 of endoscopic portion 14 and the forward end of support member 20 is positioned within channel 134. The three components namely, endoscopic portion 14, sleeve member 128 and support member 20 are connected to each other via a connecting pin 136 which is inserted within correspondingly positioned apertures provided in each of the three components.

Thus, support member 20 articulates in response to axial movement of rod member 120 which is controlled by rotational movement of control knob 24. Support member 20 is capable of incrementally pivoting between a position in general alignment with the longitudinal axis defined by endoscopic portion 14 and a position about 130° relative to the axis, and any number of angular positions therebetween. Although shown in FIG. 1 having a maximum angular position of approximately 130°, other maximum angles of articulation are contemplated. Channel 134 of sleeve member 128 and a partial slot 138 formed in distal end portion 18 of endoscopic portion 14 permit support member to pivot i.e. articulate, through its full range of motion. FIGS. 9 and 10 illustrate the range of articulation of support member 20 in detail.

In use, the apparatus is inserted into the uterus and control knob 24 is rotated to articulate the distal end position to the desired position. Inflation control knob 22 is then rotated to controllably inflate the balloon to the desired dimension This effectively restrains the uterus from movement during the surgical procedure and retains the instrument in the cavity.

Figure 11:
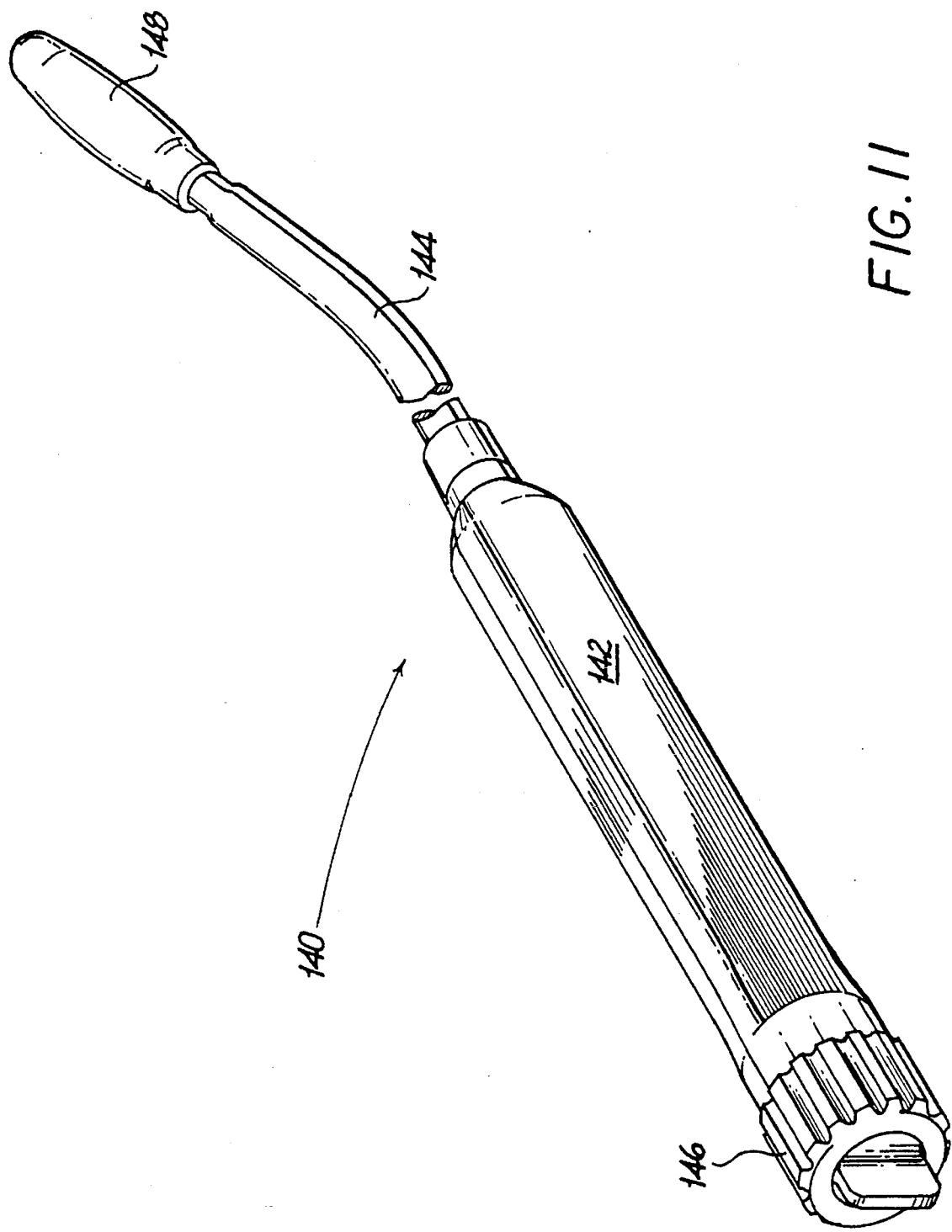
FIG. 11 is an alterative embodiment of the apparatus of the present invention having a curved endoscopic portion.
Figure 12A:
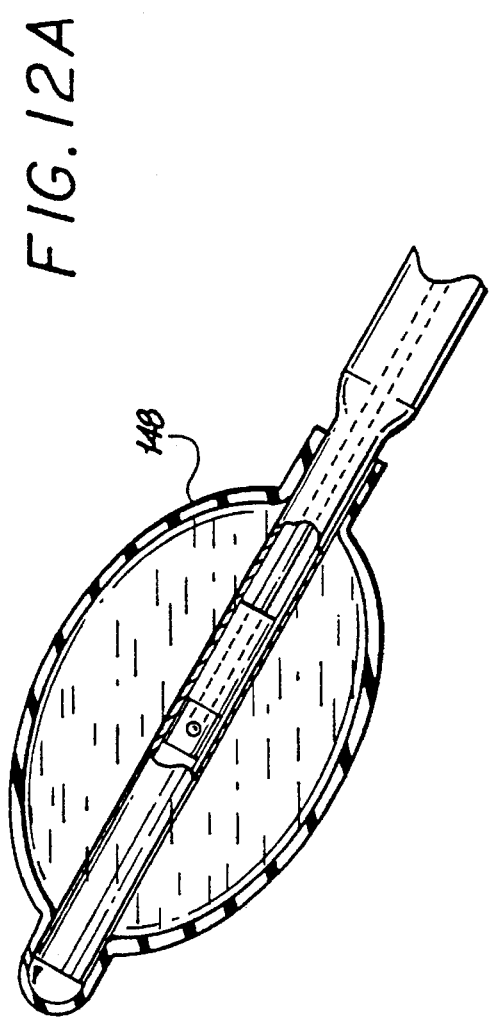
Figure 12B:
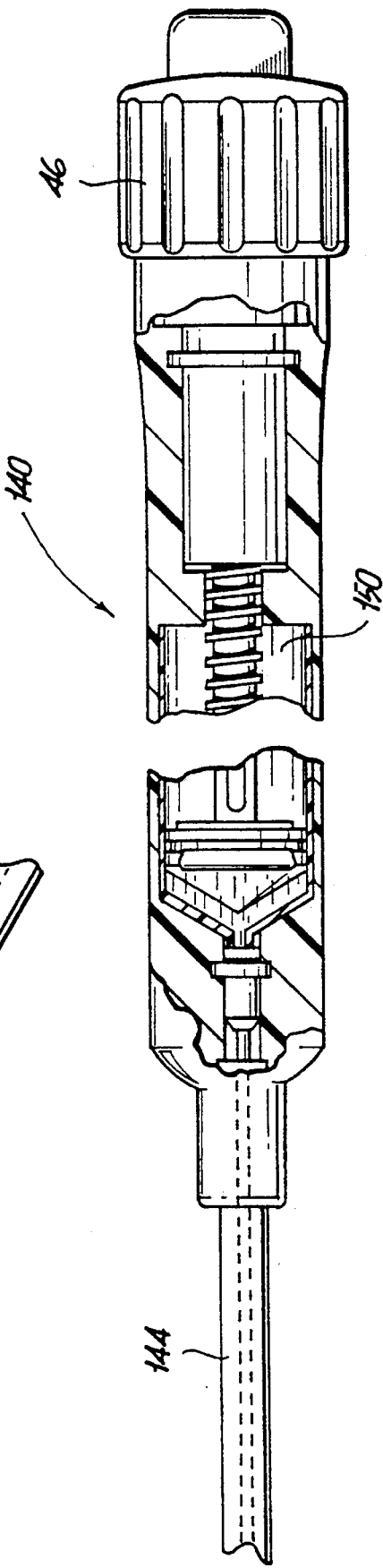
FIG. 12B is a cross-sectional view of the handle of the apparatus of FIG. 11.

Referring now to FIGS. 11, 12A and 12B, an alterative embodiment of the present invention is illustrated in which the endoscopic portion is curved to accommodate the body curvature. Apparatus 140 includes handle 142, elongated member 144 portion extending distally at the handle and control knob 146 rotatably mounted to the handle. Control knob 146 controls expansion of the expandable member 148 in a manner identical to the embodiment of FIG. 1 and includes a ratchet mechanism and a release mechanism for releasing the ratchet mechanism similar in construction and function to the aforedescribed embodiment. Handle 142 includes a plunger assembly 150 which is substantially similar to the plunger assembly disclosed in connection with the embodiment of FIG. 1. In accordance with this embodiment, elongated member 144 is slightly arcuately-shaped to follow the natural curvature of the uterine cavity to thereby facilitate insertion into the cavity. The radius of curvative is preferably 8 inches.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A surgical apparatus for manipulating body tissue, which comprises:

a handle member;

a generally elongated member connected to said handle member and extending distally therefrom, said elongated member having a longitudinal axis and including proximal and distal end portions, said distal end portion pivotally connected to said proximal end portion about a pivot pin and being pivotal about said pivot pin relative to said longitudinal axis;

an expandable member mounted to said distal end portion of said elongated member and movable upon pivotal movement of said distal end portion; and a fluid dispenser at least partially disposed within said handle member and being in fluid communication with said expandable member for selectively incrementally dispensing fluid into said expandable member to selectively incrementally inflate said expandable member.

2. Apparatus according to claim 1, wherein at least a portion of said elongated member is curved in configuration in a longitudinal direction.

3. Apparatus according to claim 2, further comprising a rotatable control knob operatively connected to said fluid dispenser for actuating said fluid dispenser to incrementally dispense fluid into said expandable member.

4. Apparatus according to claim 1, further comprising a rotatable control knob operatively connected to said fluid dispenser for actuating said fluid dispenser to incrementally dispense fluid into said expandable member.

5. A surgical apparatus, for manipulating body tissue, which comprises:

a handle member;

a generally elongated member connected to said handle member and extending distally therefrom, said elongated member having a longitudinal axis and including proximal and distal end portions, said distal end portion pivotally connected to said proximal end portion and being pivotal relative to said longitudinal axis;

a rotatable control knob rotatably mounted to said handle member for selectively pivoting said distal end portion of said elongated member relative to said longitudinal axis;

an expandable member mounted to said distal end portion of said elongated member and movable upon pivotal movement of said distal end portion; and a fluid dispenser at least partially disposed within said handle member and being in fluid communication with said expandable member for selectively incrementally dispensing fluid into said expandable member to selectively incrementally inflate said expandable member.

6. A surgical apparatus for manipulating bodily tissue, which comprises:

a handle member configured to be grasped by a user;

a generally elongated member connected to said handle member, said elongated member defining a longitudinal axis and having proximal and distal end portions;

an expandable member mounted to a support member, said support member connected to said distal end portion of said elongated member and being movable with respect to said longitudinal axis such that said expandable member is movable therewith;

a proximally located manually moveable member operatively connected to said support member, said manually moveable member moveable to cause movement of said support member; and inflating means cooperating with said expandable member for inflating said expandable member.

7. A surgical apparatus for manipulating bodily tissue, which comprises:

a handle member configured to be grasped by a user;

a generally elongated member connected to said handle member, said elongated member defining a longitudinal axis and having proximal and distal end portions;

an expandable member mounted to a support member, said support member connected to said distal end portion of said elongated member and being selectively articulatable by a control member mounted to said handle member, said control member movable to selectively articulate said support member to thereby move said expandable member; and inflating means cooperating with said expandable member for inflating said expandable member.

8. Apparatus according to claim 7, wherein said control member is rotatable about said longitudinal axis.

9. A surgical apparatus for manipulating bodily tissue, which comprises:

a frame member including a chamber for accommodating a supply of fluid and a plunger axially movable within said chamber for dispensing the fluid;

an elongated member connected to said frame member and including a lumen in communication with said chamber of said frame member, said elongated member generally defining a longitudinal axis, at least a portion of said elongated member being arcuate in configuration in a longitudinal direction;

an expandable member mounted to a distal end portion of said elongated member and in communication with said lumen; and plunger advancing means for selectively incrementally advancing said plunger within said chamber to dispense fluid through said lumen and into said expandable member to selectively incrementally inflate said expandable member.

10. The apparatus according to claim 9 wherein said plunger advancing means is actuated by a control knob rotatably mounted to said frame member and operatively connected to said plunger such that rotational movement of said control knob in first and second directions thereof causes corresponding respective distal and proximal axial movement of said plunger.

11. A surgical apparatus for manipulating body tissue, which comprises:

a handle member configured and dimensioned to be grasped by a user;

a generally elongated member connected to said handle member and extending distally therefrom, said elongated member defining a longitudinal axis and having proximal and distal end portions;

an expandable member supported at said distal end portion of said elongated member;

inflating means at least partially disposed within said handle member and in fluid communication with said expandable member for inflating said expandable member;

manually rotatable control means operatively connected to said inflating means for actuating said inflating means; and ratchet means operatively engageable with said control means to permit rotational movement of said control means in a first direction to actuate said inflating means while preventing rotational movement of said control means in a second direction.

12. The apparatus according to claim 11 further comprising release means operatively engageable with said ratchet means for releasing said ratchet means to permit rotational movement of said control means in said second direction to axially move said plunger in the proximal direction.

13. The apparatus according to claim 12 wherein said ratchet means includes a ratchet member and associated pawl member.

14. The apparatus according to claim 13 wherein said release means comprises a release member rotatably mounted to said handle member and engagable with said pawl member wherein rotational movement of said release member through a first angular sector of rotation causes said pawl member to move to a disengaged position disengaged from said ratchet member.

15. The apparatus according to claim 14 wherein said release member is configured to permit said pawl member to return to an engaged position in engagement with said ratchet member upon rotation of said release member through a second angular sector of rotation.

16. The apparatus according to claim 11 wherein said expandable member is mounted to a support member pivotally connected to said distal end portion of said elongated member, said support member being pivotable relative to a longitudinal axis defined by said elongated member such that said expandable member is pivotal therewith.

17. The apparatus according to claim 16 wherein said support member is selectively pivotable to a number of angular positions with respect to said longitudinal axis.

18. The apparatus according to claim 16 further comprising pivotal control means operatively connected to said support member to pivot said support member from a proximal location.

19. The apparatus according to claim 18 wherein said pivotal control means is disposed at a proximal end portion of said elongated member.

20. The apparatus according to claim 19 wherein said pivotal control means comprises a rotatable member mounted about said proximal end portion of said elongated member.

21. The apparatus according to claim 20 wherein said rotatable member is operatively connected to an elongated control rod positioned within said elongated member, wherein rotational movement of said rotatable member in a first direction causes longitudinal movement of said elongated control rod in a proximal direction and wherein rotational movement of said rotatable member in a second direction causes longitudinal movement of said elongated control rod in a distal direction.

22. The apparatus according to claim 21 wherein said elongated control rod is operatively connected to said support member such that longitudinal movement of said elongated control rod in the proximal and distal directions causes corresponding pivotal movement of said support member.

23. The apparatus according to claim 20 wherein said rotatable member comprises a cylindrical control sleeve rotatably mounted about a proximal end portion of said elongated member.

24. The apparatus according to claim 19 wherein said support member is adapted to pivot between a first position at substantially zero degrees with respect to said longitudinal axis defined by said elongated member and a second position at about 130 degrees with respect to said longitudinal axis and at least one intermediate position between said first and second positions.

25. The apparatus according to claim 13 wherein at least a portion of said elongated member is generally arcuate in configuration in a longitudinal direction.

26. The apparatus according to claim 25 further comprising means operatively engagable with said ratchet means for releasing said ratchet means to permit movement of said control means in said second direction to deactivate said inflating means.

27. The apparatus according to claim 11 wherein said expandable member is mounted to said distal end portion of said elongated member.

* * * * *